(12) United States Patent
Li et al.

(10) Patent No.: US 10,350,074 B2
(45) Date of Patent: Jul. 16, 2019

(54) PATIENT-SPECIFIC MANUFACTURING OF POROUS METAL PROSTHESES

(71) Applicant: Zimmer, Inc., Warsaw, IN (US)

(72) Inventors: Jia Li, Fort Wayne, IN (US); Scott V. Cron, Wayne, NJ (US); Jeffrey Bassett, Jupiter, FL (US); Edward M. Willis, Hoboken, NJ (US)

(73) Assignee: Zimmer, Inc., Warsaw, IN (US)

( * ) Notice: Subject to any disclaimer, the term of this patent is extended or adjusted under 35 U.S.C. 154(b) by 65 days.

(21) Appl. No.: 15/495,115

(22) Filed: Apr. 24, 2017

(65) Prior Publication Data

US 2017/0224494 A1 Aug. 10, 2017

Related U.S. Application Data

(62) Division of application No. 13/464,069, filed on May 4, 2012, now Pat. No. 9,662,214.

(Continued)

(51) Int. Cl.
*A61F 2/30* (2006.01)
*B33Y 80/00* (2015.01)
(Continued)

(52) U.S. Cl.
CPC ........ *A61F 2/30942* (2013.01); *A61F 2/2803* (2013.01); *A61F 2/30767* (2013.01); *B29C 33/3842* (2013.01); *B29C 64/106* (2017.08); *B29C 64/386* (2017.08); *B33Y 10/00* (2014.12); *B33Y 50/02* (2014.12); *B33Y 80/00* (2014.12); *C23C 16/06* (2013.01); *C23C 16/44* (2013.01); *A61F 2/44* (2013.01); *A61F 2002/3092* (2013.01); *A61F 2002/3093* (2013.01); *A61F 2002/3096* (2013.01); *A61F 2002/30952* (2013.01); *A61F 2002/30957* (2013.01); *A61F 2002/30962* (2013.01); *A61F 2002/30963* (2013.01); *A61F 2002/30985* (2013.01);

(Continued)

(58) Field of Classification Search
CPC ...................................................... B29C 35/08
USPC ........................................................ 264/219
See application file for complete search history.

(56) References Cited

U.S. PATENT DOCUMENTS 5,282,861 A 2/1994 Kaplan
5,768,134 A 6/1998 Swaelens et al.
(Continued)

FOREIGN PATENT DOCUMENTS

EP 0622052 A1 11/1994
EP 2272461 A2 1/2011
(Continued)

OTHER PUBLICATIONS

Stryker Corporation, [Online] Retrieved From Internet: <www.porexsurgical.com/product/medpor-implants>, (2011).
(Continued)

*Primary Examiner* — Dah-Wei D. Yuan
*Assistant Examiner* — Andrew J Bowman
(74) *Attorney, Agent, or Firm* — Schwegman Lundberg & Woessner, P.A.

(57) ABSTRACT

A patient-specific porous metal prosthesis and a method for manufacturing the same are provided. The orthopedic prosthesis may be metallic to provide adequate strength and stability. Also, the orthopedic prosthesis may be porous to promote bone ingrowth.

18 Claims, 9 Drawing Sheets

Related U.S. Application Data (60) Provisional application No. 61/483,502, filed on May 6, 2011.

(51) Int. Cl.

| | | |
|---|---|---|
| *A61F 2/28* | (2006.01) |
| *B33Y 10/00* | (2015.01) |
| *B33Y 50/02* | (2015.01) |
| *B29C 33/38* | (2006.01) |
| *C23C 16/06* | (2006.01) |
| *C23C 16/44* | (2006.01) |
| *B29C 64/106* | (2017.01) |
| *B29C 64/386* | (2017.01) |
| *A61F 2/44* | (2006.01) |
| *B29L 31/00* | (2006.01) |

(52) U.S. Cl.
CPC ........... *A61F 2310/00011* (2013.01); *B29L 2031/7532* (2013.01); *F04C 2270/041* (2013.01)

(56) References Cited

U.S. PATENT DOCUMENTS

| | | | |
|---|---|---|---|
| 9,662,214 B2 | 5/2017 | Li et al. | |
| 2005/0133955 A1* | 6/2005 | Christensen | A61C 13/0004 264/219 |
| 2007/0055373 A1 | 3/2007 | Hudgins et al. | |
| 2007/0077267 A1* | 4/2007 | Molz, IV | A61L 27/227 424/423 |
| 2011/0106093 A1 | 5/2011 | Romano et al. | |
| 2012/0310364 A1 | 12/2012 | Li et al. | |

FOREIGN PATENT DOCUMENTS

| | | | |
|---|---|---|---|
| EP | 2465549 A1 | 6/2012 |
| WO | WO-2012154534 A1 | 11/2012 |

OTHER PUBLICATIONS

Beckman Institute for Advanced Science and Technology at the University of Illinois, [Online] Retrieved From Internet: <www.itg.uiuc.edu/technology/reconstruction>, (2005).

"U.S. Appl. No. 13/464,069, Final Office Action dated Feb. 12, 2016", 10 pgs.

"U.S. Appl. No. 13/464,069, Non Final Office Action dated Jul. 1, 2016", 11 pgs.

"U.S. Appl. No. 13/464,069, Non Final Office Action dated Aug. 5, 2015", 9 pgs.

"U.S. Appl. No. 13/464,069, Notice of Allowance dated Jan. 25, 2017", 8 pgs.

"U.S. Appl. No. 13/464,069, Response filed May 12, 2016 to Final Office Action dated Feb. 12, 2016", 10 pgs.

"U.S. Appl. No. 13/464,069, Response filed Sep. 29, 2016 to Non Final Office Action dated Jul. 1, 2016", 10 pgs.

"U.S. Appl. No. 13/464,069, Response filed Nov. 5, 2015 to Non Final Office Action dated Aug. 5, 2015", 9 pgs.

"U.S. Appl. No. 13/464,069, Response filed Nov. 19, 2014 to Restriction Requirement dated Sep. 23, 2014", 6 pgs.

"U.S. Appl. No. 13/464,069, Restriction Requirement dated Sep. 23, 2014", 6 pgs.

"European Application Serial No. 12721116.7, Communication Pursuant to Article 94(3) EPC dated Apr. 6, 2016", 4 pgs.

"European Application Serial No. 12721116.7, Response filed Jul. 31, 2014 to Communication pursuant to Rules 161(1) and 162 EPC dated Jan. 22, 2014", 9 pgs.

"European Application Serial No. 12721116.7, Response filed Aug. 16, 2016 to Communication Pursuant to Article 94(3) EPC dated Apr. 6, 2016", 7 pgs.

"International Application Serial No. PCT/US2012/036467, International Preliminary Report on Patentability dated Nov. 21, 2013", 8 pgs.

"International Application Serial No. PCT/US2012/036467, International Search Report and Written Opinion dated Jul. 20, 2012", 12 pgs.

"Zimmer Trabecular Metal Acetabular Revision System", 97-7255-049-00 5ML, (2007), 16 pgs.

Jenkins, et al., "The Fabrication of Artifacts out of Glassy Carbon and Carbon-Fiber-Reinforced Carbon for Biomedical Applications", Journal of Biomedical Materials Research, vol. 13, (1979), 371-394.

Medlin, et al., "Metallurgical Characterization of a Porous Tantalum Biomaterial (Trabecular Metal) for Orthopaedic Implant Applications", Medical Devices Materials: Proceedings of the Materials & Processes for Medical Devices Conference, [Online] Retrieved From Internet <ftp://ftp.sheridan.com/pub/reprintseproof/040FS/172163Medlin.PDF>, (Mar. 2, 2011), 394-398.

"European Application Serial No. 12721116.7, Office Action dated May 29, 2018", 5 pgs.

U.S. Appl. No. 13/464,069, filed May 4, 2012, Patient-Specific Manufacturing of Porous Metal Prostheses.

* cited by examiner

PATIENT-SPECIFIC MANUFACTURING OF POROUS METAL PROSTHESES

CROSS-REFERENCE TO RELATED APPLICATIONS

This application is a divisional of U.S. patent application Ser. No. 13/464,069, filed May 4, 2012, which claims the benefit of priority from U.S. Provisional Patent Application Ser. No. 61/483,502, filed May 6, 2011, the disclosures of which are hereby expressly incorporated by reference herein in their entirety.

FIELD OF THE DISCLOSURE

The present disclosure relates to porous metal prostheses. More particularly, the present disclosure relates to patient-specific porous metal prostheses, and to a method for manufacturing the same.

BACKGROUND OF THE DISCLOSURE

Orthopaedic prostheses are commonly used to replace at least a portion of a patient's bone following traumatic injury or deterioration due to aging, illness, or disease, for example.

When the orthopaedic prosthesis is implanted into a joint, the orthopaedic prosthesis may be configured to articulate with an adjacent orthopaedic component. For example, when the orthopaedic prosthesis is implanted into the patient's hip joint, the orthopaedic prosthesis may be socket-shaped to receive and articulate with an adjacent femoral component.

The orthopaedic prosthesis may be at least partially porous to promote ingrowth of the patient's surrounding bone and/or soft tissue, which may enhance the fixation between the orthopaedic prosthesis and the patient's surrounding bone and/or soft tissue. Although porous polymers may be used in certain circumstances, porous metals provide additional strength and stability to the orthopaedic prosthesis.

SUMMARY

The present disclosure provides a patient-specific orthopaedic prosthesis and a method of manufacturing the same. The orthopaedic prosthesis may be metallic to provide adequate strength and stability. Also, the orthopaedic prosthesis may be porous to promote bone ingrowth. The orthopaedic prosthesis may be implanted anywhere in the musculoskeletal system including, but not limited to, the hip, knee, spine, extremities, cranium, or mandible to provide fixation of bone or to replace an articulating surface of a joint.

According to an embodiment of the present invention, a method is provided for manufacturing a customised orthopaedic prosthesis comprising the following steps: capturing at least one image of a patient's bone; transforming the at least one image into electronic information; utilizing the electronic information to create a three-dimensional model of the bone; using the bone model to create a model of a customised orthopaedic prosthesis; forming a mold based on the customised model of the prosthesis; and fabricating the prosthesis in the mold to have the size and shape of the customised model.

In the first step of the method, preferably a surgeon or another party captures image data of a patient's bone or damaged bone. The damaged bone may include all or part of the patient's maxilla, mandible, or another craniofacial bone. The damaged bone may also include all or part of the patient's femur, tibia, pelvis, humerus, or scapula, for example. The image data may be captured using a suitable imaging modality, such as X-ray, fluoroscopy, magnetic resonance imaging (MRI), computed tomography (CT), or ultrasound, for example. The image data may include two-dimensional views of the damaged bone, three-dimensional views of the damaged bone, or combinations thereof.

Continuing to the next step of the method, the surgeon or another party preferably uses the previously-captured image data to generate a three-dimensional model of the bone. The bone model may be a digital model that is generated using a suitable computer planning system. The computer planning system may be programmed to combine, evaluate, and process the image data. For example, the computer planning system may be programmed to combine a plurality of two-dimensional X-ray images to generate the three-dimensional bone model. In certain embodiments, the computer planning system includes image processing software that is able to segment, or differentiate, desired anatomic structures (e.g., bone tissue) from undesired structures (e.g., surrounding soft tissue) in the image data.

In the next step, the surgeon or another party uses the bone model to design a model of a custom, patient-specific orthopaedic prosthesis having a desired shape. In certain embodiments, the prosthesis model is designed to replicate a portion of the bone model that will be resected. For example, if the bone model includes a fractured, diseased, or weakened area of the patient's bone that will be resected, the prosthesis model may be sized and shaped to replicate that fractured, diseased, or weakened area of the patient's bone. In cases of severe damage to the patient's bone when the entire bone will be resected, the prosthesis model may be designed to replicate the entire bone model. In other embodiments, the prosthesis model is designed to fill in a missing portion of the bone model. For example, if an area of the patient's bone is missing due to disease or traumatic injury, the prosthesis model may be sized and shaped to fill in that missing area of the patient's bone. It is understood that the prosthesis may be designed to perform both functions—replicating all or a portion of the patient's bone that will be resected and also filling in a missing portion of the patient's bone.

The prosthesis model may be a digital model that is designed using a suitable computer planning system having, for example, computer-aided design (CAD) software. The computer planning system may allow the designer to define or specify certain boundaries of the prosthesis model. For example, the computer planning system may allow the designer to define or specify the shape of an exposed surface or an articulating surface of the prosthesis model. The computer planning system may automatically define other boundaries of the prosthesis model. For example, the computer planning system may automatically define the shape of a bone-contacting surface of the prosthesis model as substantially a negative of the bone model so that the prosthesis model conforms to the bone model and is perfectly contoured to fit against the bone model. In this manner, once manufactured, a patient-specific, bone-contacting surface of the orthopaedic prosthesis may also be shaped as substantially a negative of the patient's bone such that the patient-specific surface of the orthopaedic prosthesis conforms to the patient's bone and is perfectly contoured to fit against the patient's bone, even a substantially uncut or unreamed surface of the patient's bone that is highly irregular, arbitrary, non-parametric, or biologically complex. The computer planning system may also allow the designer to add sockets, channels, recesses, or other features to the prosthesis model, thereby allowing the orthopaedic prosthesis to receive suitable fasteners (e.g., bone screws) or tools, for example. In summary, the computer planning system allows the designer to accommodate the needs of the particular patient when designing the prosthesis model.

The prosthesis model represents a custom, patient-specific orthopaedic prosthesis having a desired shape. Because the prosthesis model is designed based on the traumatic injury or deterioration suffered by the particular patient and the surrounding anatomy of the particular patient, the desired shape of the prosthesis model may be highly irregular, arbitrary, and biologically complex, especially when the orthopaedic prosthesis represented by the prosthesis model will be used for a geometrically demanding application. In certain embodiments, the prosthesis model may lack any planes of symmetry.

In the next step, the surgeon or another party uses the prosthesis model to form a custom, patient-specific mold. In one embodiment, the mold is formed by a rapid manufacturing process to define a negative space that corresponds in size and shape to the prosthesis model. In another embodiment, the mold is formed by casting the mold around a template that corresponds in size and shape to the prosthesis model.

It is within the scope of the present disclosure that the steps of the method may be performed by different parties.

According to a further embodiment of the present invention, a further method is provided for manufacturing a patient-specific orthopaedic prosthesis. The method includes the steps of: manufacturing a patient-specific mold; placing a porous substrate in the patient-specific mold, the porous substrate having a plurality of struts that define pores of the porous substrate; shaping the porous substrate with the patient-specific mold; and after the shaping step, coating the plurality of struts of the porous substrate with a biocompatible metal.

According to another embodiment of the present invention, a method is provided for manufacturing a patient-specific orthopaedic prosthesis using a prosthesis model that is shaped to represent the patient-specific orthopaedic prosthesis. The method includes the steps of: manufacturing a patient-specific mold that defines a negative space, the negative space of the patient-specific mold corresponding in shape to the prosthesis model; selecting a porous substrate having a plurality of struts that define pores of the porous substrate, the porous substrate having a first shape; operating the patient-specific mold to change the first shape of the porous substrate to a second shape that differs from the first shape, the second shape of the porous substrate corresponding to the prosthesis model; and after the operating step, coating the plurality of struts of the porous substrate with a biocompatible metal.

According to yet another embodiment of the present invention, a patient-specific orthopaedic prosthesis is provided that is configured to be implanted against a surface of a particular patient's bone. The orthopaedic prosthesis includes a porous substrate having a plurality of struts that define pores of the porous substrate and a biocompatible metal coating the plurality of struts of the porous substrate, the orthopaedic prosthesis having a patient-specific surface that is shaped as substantially a negative of the surface of the particular patient's bone such that the patient-specific surface of the orthopaedic prosthesis conforms to the surface of the particular patient's bone.

The step of manufacturing a patient specific mold according to the methods of the invention preferably creates a negative space in the mold sized and shaped to substantially match the size and shape of the prosthesis model.

The mold may includes a top or first portion and a bottom or second portion that cooperate to define an interior, negative space that matches the size and shape of prosthesis model. Although the mold will preferably comprise a two-piece component, it is also within the scope of the present disclosure that the mold may include three, four, five, or more pieces. The portions of the mold may include corresponding pegs and recesses to guide the portions of the mold into proper alignment.

In certain embodiments, the mold may be manufactured using a rapid subtractive manufacturing process, wherein material is machined away from a bulk structure to arrive at the final mold structure. In other embodiments, the mold can be manufactured using a rapid additive manufacturing process, wherein material is laid down layer by layer to build the final mold structure. In still other embodiments, the mold is manufactured by casting material around a template to arrive at the final mold structure. The template may have substantially the same size and shape as the prosthesis model.

After manufacturing the mold, the implant manufacturer or another party may select a shapeable substrate to place in the mold. An exemplary shapeable substrate may have friable or brittle struts that are readily crushed or broken when the substrate is compressed in the mold such that the struts become located outside the negative space of the mold. An exemplary friable substrate is a porous substrate such as a reticulated vitreous carbon (RVC) structure having a large plurality of vitreous carbon struts in the form of ligaments that define open-cells or pores therebetween. The RVC structure may be produced by pyrolyzing an open-cell polymer foam.

The implant manufacturer or another party then shapes the shapeable substrate in the mold. Shaping the substrate may involve closing the mold around the substrate until the substrate takes on the shape of the mold's negative space, which also corresponds to the shape of the prosthesis model.

According to a preferred embodiment of the invention, the substrate is shaped in the mold by breakage, deformation, and/or crushing. The deformation that occurs during the shaping step is preferably minimized for efficiency and to avoid substantially changing the porosity of the structure. The amount of breakage, deformation, and/or crushing may be minimized by designing the mold to compress the structure in multiple, non-parallel directions.

After shaping, the substrate may be coated for example by a chemical vapor deposition (CVD) process. The coating step may strengthen the substrate for implantation, causing the substrate to become less readily shapeable than before the coating step.

The orthopaedic prosthesis produced by methods of the invention may be a highly porous metallic structure, such as a highly porous tantalum structure, which may have a porosity as low as 55%, 65%, or 75% and as high as 80%, 85%, or 90%. Generally, the highly porous tantalum structure includes a large plurality of struts in the form of ligaments defining open-cells or pores therebetween, with each ligament generally including a vitreous carbon core covered by a thin film of tantalum metal. The open-cells between the ligaments form a matrix of continuous channels having no dead ends, such that growth of cancellous bone through the porous tantalum structure is uninhibited. The porous tantalum structure may be made in a variety of densities in order to selectively tailor the structure for particular applications.

According to still yet another embodiment of the present invention, a method is provided for manufacturing a patient-specific orthopaedic prosthesis using a prosthesis model that is shaped to represent the patient-specific orthopaedic prosthesis. The method includes the steps of: performing a rapid manufacturing process to manufacture a template corresponding to the prosthesis model, manufacturing a patient-specific mold around the template, the patient-specific mold defining a negative space that corresponds in shape to the template and to the prosthesis model, and inserting a biocompatible material into the patient-specific mold to produce the patient-specific orthopaedic prosthesis.

The template is manufactured having substantially the same size and shape as the prosthesis model. The template may be manufactured of a polymer, metal, or another suitable material.

A custom, patient-specific mold is made using the template. For example, the mold itself is manufactured by a casting or molding process, with the template defining the interior shape of the mold and another template defining the exterior shape of the mold. Forming elements like pins and dividers may also be used to add openings, injection ports, and other features to the mold. When the templates and other forming elements are separated from the newly cast mold, the negative space of the mold will be sized and shaped to match the template and the prosthesis model Next, the implant manufacturer fills the mold with a biocompatible material to produce a custom, patient-specific orthopaedic prosthesis. The filling step may involve an injection molding process, for example. In one embodiment, the biocompatible material used in the molding step is a metal. Suitable metals include, for example, titanium, tantalum, cobalt chromium, cobalt chromium molybdenum, and alloys thereof.

In another embodiment, the biocompatible material used in the molding step is a polymer. The polymer may be pre-polymerized before being injected into the mold. Such pre-polymerized materials include, for example, polyurethane, polystyrene, polypropylene, polyethylene, and polyoxymethylene. Alternatively, unpolymerized materials may be injected into the mold with polymerization occurring in the mold. Such unpolymerized materials include polyisocyanates and polyols, for example, which will react in the mold to form a polymer. For added strength, the polymer may be further processed and coated with metal following the molding step.

To produce a porous orthopaedic prosthesis, a void former may be used during the molding step. The void former may include, for example, removable grains or particles, a blowing agent, or a chemical reactant. The void former will leave behind spaces or pores in the orthopaedic prosthesis.

The biocompatible material that is inserted into the mold may also be a shapeable substrate that is shaped in the mold by breakage, deformation, and/or crushing.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
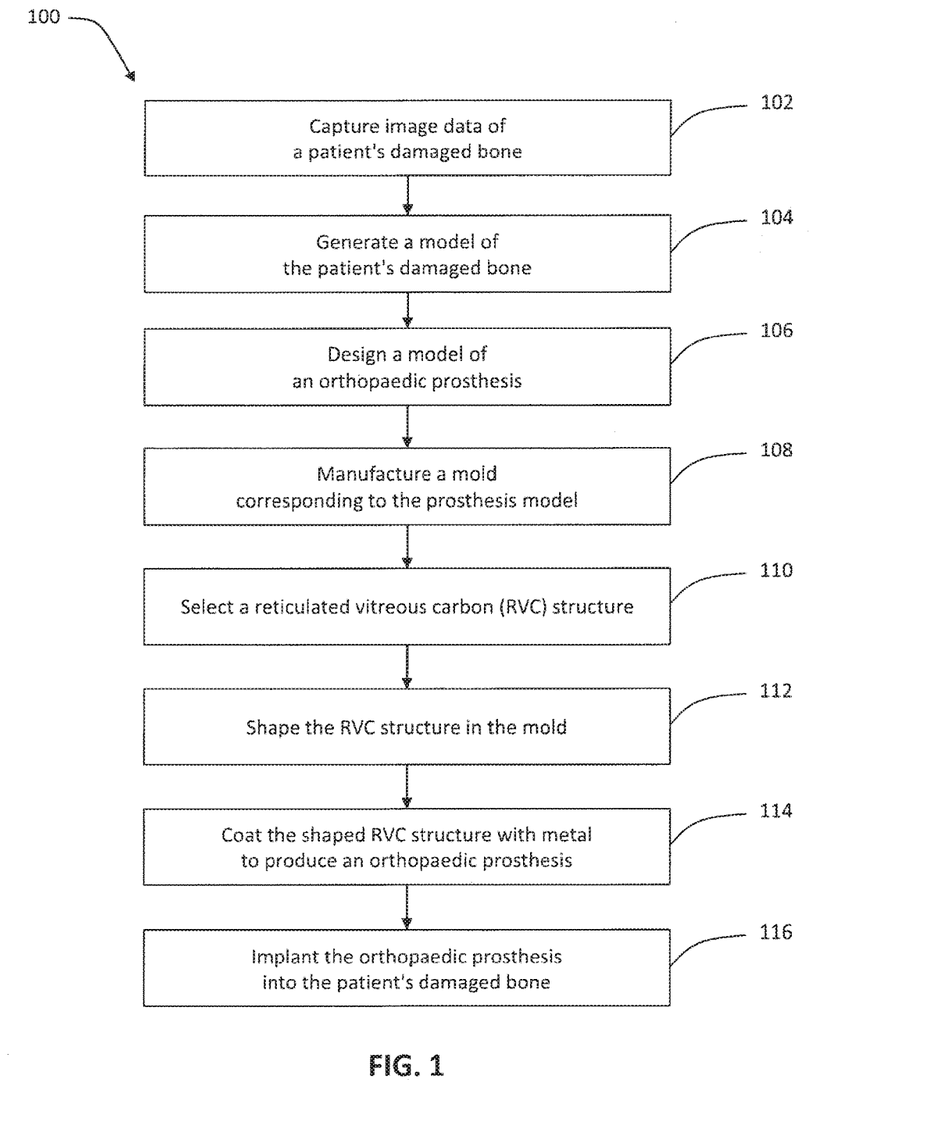
FIG. 1 is a flow chart of an exemplary method for designing and manufacturing a patient-specific porous metal prosthesis.

FIG. 1 provides an exemplary method 100 for designing and manufacturing a patient-specific porous metal prosthesis. Method 100 is exemplified with reference to FIGS. 2-9.

Beginning at step 102 of method 100 (FIG. 1), a surgeon or another party captures image data of a patient's damaged bone. The damaged bone may include all or part of the patient's maxilla, mandible, or another craniofacial bone. The damaged bone may also include all or part of the patient's femur, tibia, pelvis, humerus, or scapula, for example. The image data may be captured using a suitable imaging modality, such as X-ray, fluoroscopy, magnetic resonance imaging (MRI), computed tomography (CT), or ultrasound, for example. The image data may include two-dimensional views of the damaged bone, three-dimensional views of the damaged bone, or combinations thereof.

Figure 2:
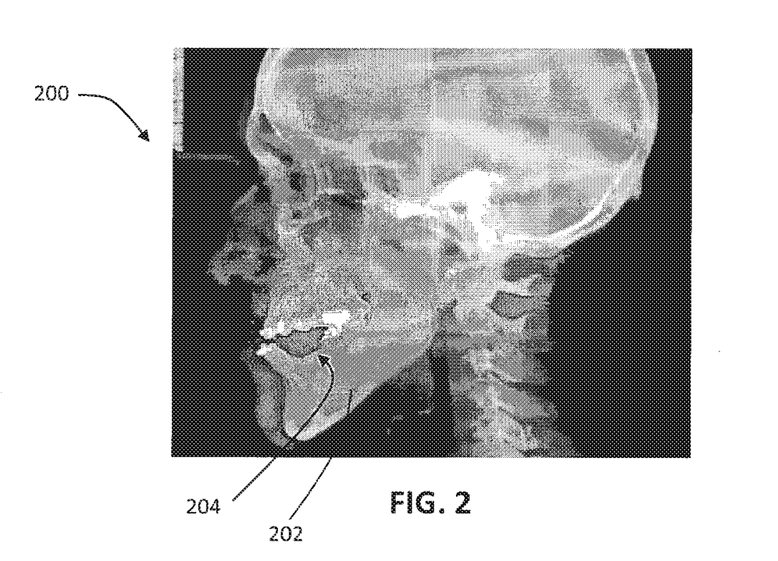
FIG. 2 is an X-ray of a patient's jaw showing the patient's damaged mandible.

With reference to FIG. 2, for example, X-ray image 200 is captured showing the patient's damaged mandible 202 or lower jaw bone. In this example, the patient has suffered bone loss in area 204 of mandible 202.

Continuing to step 104 of method 100 (FIG. 1), the surgeon or another party uses the previously-captured image data from step 102 to generate a three-dimensional model of the damaged bone. The bone model may be a digital model that is generated using a suitable computer planning system. The computer planning system may be programmed to combine, evaluate, and process the image data from step 102. For example, the computer planning system may be programmed to combine a plurality of two-dimensional X-ray images from step 102 to generate the three-dimensional bone model of step 104. In certain embodiments, the computer planning system includes image processing software that is able to segment, or differentiate, desired anatomic structures (e.g., bone tissue) from undesired structures (e.g., surrounding soft tissue) in the image data. For example, the image processing software may assign a grey value to each pixel of the image data, set a threshold grey value, and segment desired pixels from undesired pixels based on the threshold grey value, as discussed in U.S. Pat. No. 5,768,134 to Swaelens et al., the disclosure of which is expressly incorporated herein by reference.

Figure 3:
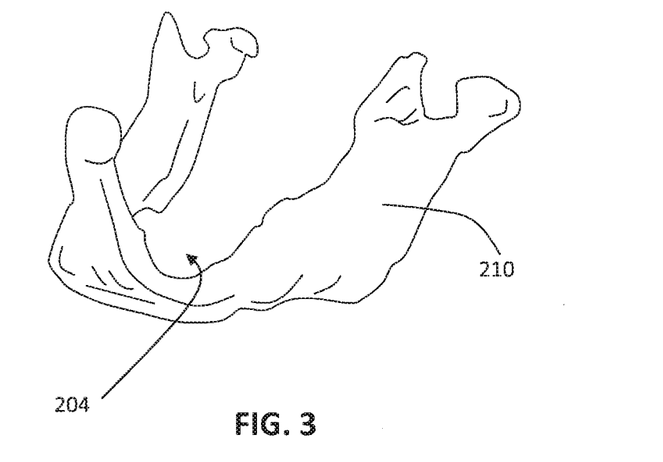
FIG. 3 is a perspective view of a bone model of the patient's damaged mandible.

With reference to FIG. 3, for example, a three-dimensional bone model 210 is shown which replicates the patient's damaged mandible 202 (FIG. 2). Bone loss area 204 is visible in bone model 210.

In step 106 of method 100 (FIG. 1), the surgeon or another party uses the bone model from step 104 to design a model of a custom, patient-specific orthopaedic prosthesis having a desired shape. In certain embodiments, the prosthesis model is designed to replicate a portion of the bone model that will be resected. For example, if the bone model includes a fractured, diseased, or weakened area of the patient's bone that will be resected, the prosthesis model may be sized and shaped to replicate that fractured, diseased, or weakened area of the patient's bone. In cases of severe damage to the patient's bone when the entire bone will be resected, the prosthesis model may be designed to replicate the entire bone model. In other embodiments, the prosthesis model is designed to fill in a missing portion of the bone model. For example, if an area of the patient's bone is missing due to disease or traumatic injury, the prosthesis model may be sized and shaped to fill in that missing area of the patient's bone. It is understood that the prosthesis may be designed to perform both functions—replicating all or a portion of the patient's bone that will be resected and also filling in a missing portion of the patient's bone.

Like the bone model from step 104, the prosthesis model from step 106 of method 100 (FIG. 1) may be a digital model that is designed using a suitable computer planning system having, for example, computer-aided design (CAD) software. The computer planning system may allow the designer to define or specify certain boundaries of the prosthesis model. For example, the computer planning system may allow the designer to define or specify the shape of an exposed surface or an articulating surface of the prosthesis model. The computer planning system may automatically define other boundaries of the prosthesis model. For example, the computer planning system may automatically define the shape of a bone-contacting surface of the prosthesis model as substantially a negative of the bone model so that the prosthesis model conforms to the bone model and is perfectly contoured to fit against the bone model. In this manner, once manufactured, a patient-specific, bone-contacting surface of the orthopaedic prosthesis may also be shaped as substantially a negative of the patient's bone such that the patient-specific surface of the orthopaedic prosthesis conforms to the patient's bone and is perfectly contoured to fit against the patient's bone, even a substantially uncut or unreamed surface of the patient's bone that is highly irregular, arbitrary, non-parametric, or biologically complex. The computer planning system may also allow the designer to add sockets, channels, recesses, or other features to the prosthesis model, thereby allowing the orthopaedic prosthesis to receive suitable fasteners (e.g., bone screws) or tools, for example. In summary, the computer planning system allows the designer to accommodate the needs of the particular patient when designing the prosthesis model.

Figure 4:
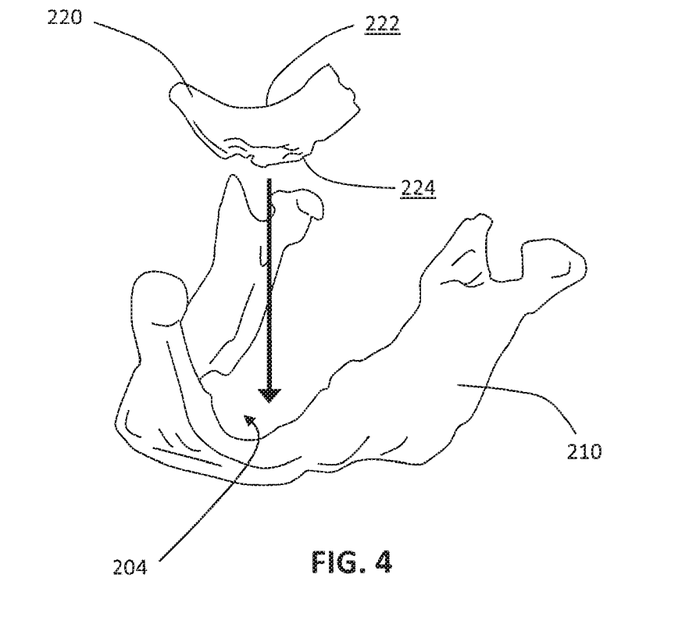
FIG. 4 is a perspective view similar to FIG. 3, also showing a prosthesis model.
Figure 5:
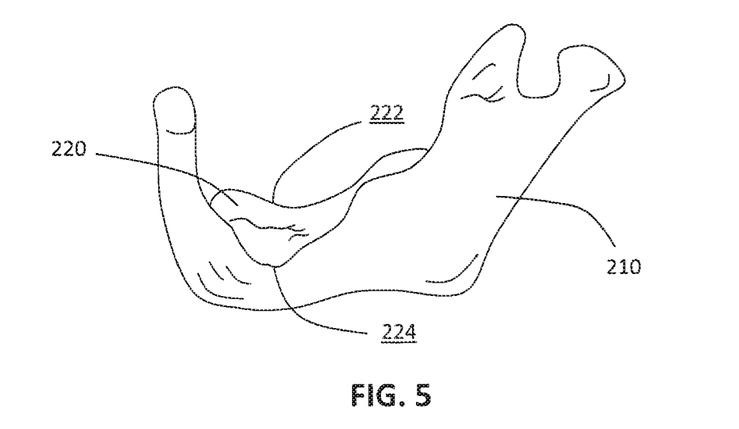
FIG. 5 is an elevational view of the bone model and the prosthesis model of FIG. 4.

With reference to FIGS. 4 and 5, for example, prosthesis model 220 is designed to fill in bone loss area 204 of bone model 210. The illustrative prosthesis model 220 includes a proximal, exposed surface 222 and a distal, bone-contacting surface 224. Bone-contacting surface 224 may be a patient-specific surface having a shape that is automatically defined as substantially a negative of bone model 210 so that bone-contacting surface 224 of prosthesis model 220 conforms to bone model 210 and is perfectly contoured to fit against bone model 210, as shown in FIG. 5.

The prosthesis model from step 106 of method 100 (FIG. 1) represents a custom, patient-specific orthopaedic prosthesis having a desired shape. Because the prosthesis model is designed based on the traumatic injury or deterioration suffered by the particular patient and the surrounding anatomy of the particular patient, the desired shape of the prosthesis model may be highly irregular, arbitrary, and biologically complex, especially when the orthopaedic prosthesis represented by the prosthesis model will be used for a geometrically demanding application. In certain embodiments, the prosthesis model may lack any planes of symmetry. For example, as shown in FIGS. 4 and 5, the shape of prosthesis model 220 is highly irregular and lacks any planes of symmetry. Also, all or a portion of the outer surface of the prosthesis model may be non-parametric in shape, such that the portion of the outer surface does not fall along a parametric line or curve. For example, as shown in FIGS. 4 and 5, at least bone-contacting surface 224 of prosthesis model 220 is non-parametric in shape.

It is within the scope of the present disclosure that steps 102, 104, and 106 of method 100 (FIG. 1) may be performed by different parties. For example, the surgeon may capture image data in step 102 and send the image data off-site for modeling in steps 104 and 106.

Next, in step 108 of method 100 (FIG. 1), an implant manufacturer or another party designs and manufactures a custom, patient-specific mold that will produce a part having substantially the same size and shape as the prosthesis model from step 106. Therefore, the negative space of the mold should be sized and shaped to substantially match the size and shape of the prosthesis model from step 106.

Figure 6A:
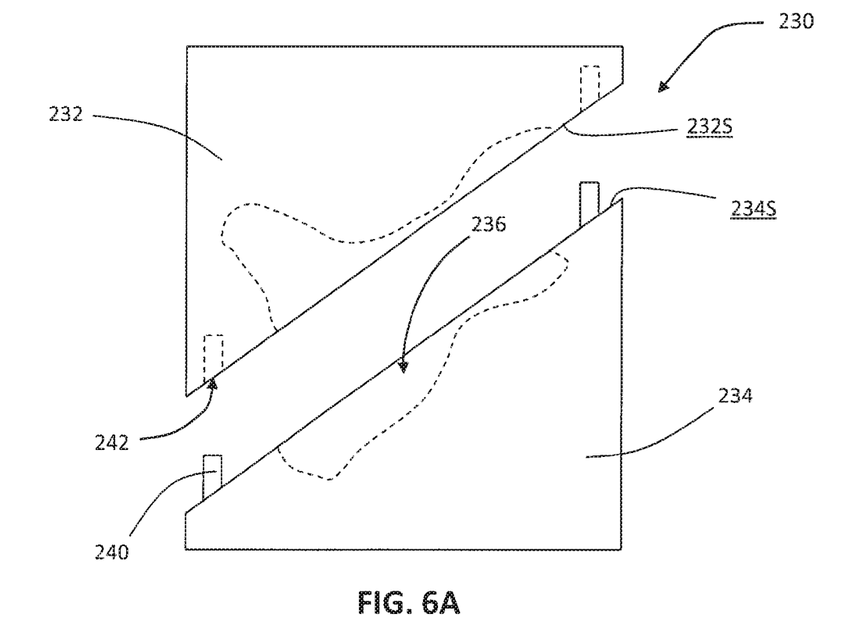
FIG. 6A is an elevational view of an exemplary mold of the present disclosure, the mold shown in an open position.
Figure 6B:
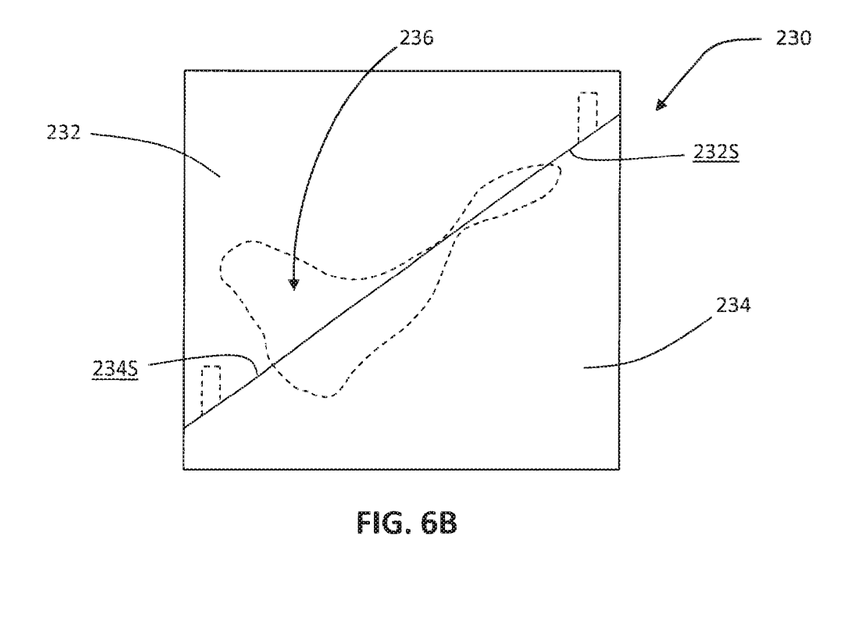
FIG. 6B is an elevational view similar to FIG. 6A, the mold shown in a closed position.

With reference to FIGS. 6A and 6B, for example, a custom, patient-specific mold 230 is provided that will produce a part having substantially the same size and shape as prosthesis model 220 (FIGS. 4 and 5). The illustrative mold 230 includes a top or first portion 232 and a bottom or second portion 234 that cooperate to define an interior, negative space 236 that matches the size and shape of prosthesis model 220. Although the illustrative mold 230 is a two-piece component, it is also within the scope of the present disclosure that mold 230 may include three, four, five, or more pieces. For example, in addition to the generally horizontal first portion 232 and the generally horizontal second portion 234, mold 230 may include a generally vertical right-side or third portion (not shown) and a generally vertical left-side or fourth portion (not shown).

Mold 230 may be designed to ensure proper alignment between first and second portions 232, 234. For example, the interfacing surfaces 232S, 234S, of first and second portions 232, 234, may be angled, as shown in FIG. 6A. If the manufacturer were to inadvertently rotate first portion 232 relative to second portion 234, for example, the interfacing surfaces 232S, 234S, would no longer fit together properly and the manufacturer would know to adjust first and second portions 232, 234, of mold 230. Additionally, first and second portions 232, 234, of mold 230 may include corresponding pegs 240 and recesses 242 to guide first and second portions 232, 234, of mold 230 into proper alignment.

Like the bone model from step 104 and the prosthesis model from step 106, the mold produced during step 108 of method 100 (FIG. 1) may be an entirely custom product that is designed and manufactured using a suitable computer planning system having, for example, computer-aided manufacturing (CAM) software. Current versions of this software incorporate a high degree of automation so little input by a designer is required.

In certain embodiments, the mold is manufactured using a rapid subtractive manufacturing process, wherein material is machined away from a bulk structure to arrive at the final mold structure. The CAM software can be used to rapidly create machine milling paths and to translate these paths into computer numerical control (CNC) code. The CNC code will drive a milling machine to rapidly cut a cavity into the bulk structure, thereby forming the negative space of the final mold structure. In other embodiments, the mold is manufactured using a rapid additive manufacturing process, wherein material is laid down layer by layer to build the final mold structure. In still other embodiments, the mold is manufactured by casting material around a template to arrive at the final mold structure. The template may have substantially the same size and shape as the prosthesis model from step 106 and may be manufactured using a rapid additive or subtractive manufacturing process, for example. When the template is removed from the newly cast mold, the negative space of the mold will be sized and shaped to match the template.

A first exemplary type of rapid additive manufacturing is 3-D printing, also known as stereolithography. 3-D printing involves feeding a liquid material through a nozzle to form a single cross-sectional layer of the final mold structure, and then exposing the material to a UV laser light to solidify the liquid material and to adhere the solidified layer onto the adjacent layer beneath. Then, a new liquid material layer is applied on top of the solidified layer, and the process is repeated until the final mold structure is completed. Alternatively, the UV laser light may be exposed to certain portions of a vat to selectively harden only those portions of the material in the vat. Then, the hardened material may be submerged in the vat and the process repeated to form a new layer on top of the hardened layer.

A second exemplary type of rapid additive manufacturing is selective laser sintering. Selective layer sintering involves exposing certain portions of a powder bed to a laser to selectively fuse together those portions of the powder and to adhere the sintered layer onto the adjacent layer beneath. Then, a new powder layer is applied on top of the sintered layer, and the process is repeated until the final mold structure is completed.

A third exemplary type of rapid additive manufacturing is fused deposition modeling. Fused deposition modeling involves laying down small, extruded beads of material layer by layer to build the final mold structure. The material may harden soon or immediately after it is extruded to adhere adjacent beads together and to adhere the extruded layer onto the adjacent layer beneath.

The above-described manufacturing methods enable construction of a custom, patient-specific mold in step 108 that will mimic the highly irregular, arbitrary, and biologically complex prosthesis model from step 106. Like the prosthesis model, the corresponding mold may lack any planes of symmetry. For example, as shown in FIGS. 6A and 6B, first and second portions 232, 234, of mold 230 are highly irregular and lack any planes of symmetry. The mold manufactured according to step 108 may also be designed to form custom features, including sockets, channels, recesses, or other custom features.

After manufacturing the mold in step 108 of method 100 (FIG. 1), the implant manufacturer or another party selects a shapeable substrate in step 110 of method 100. An exemplary shapeable substrate may have friable or brittle struts that are readily crushed or broken when the substrate is compressed in the mold such that the struts become located outside the negative space of the mold, as discussed further below. An exemplary shapeable substrate is a reticulated vitreous carbon (RVC) structure having a large plurality of vitreous carbon struts in the form of ligaments that define open-cells or pores therebetween. The RVC structure may be produced by pyrolyzing an open-cell polymer foam. During step 110 of method 100, the RVC structure may have a regular, bulk shape (e.g., a block) or a near-net shape (e.g., a partially shaped block). Also, during step 110 of method 100, the RVC structure should be at least slightly larger in size than the mold's negative space (step 108).

Figure 7:
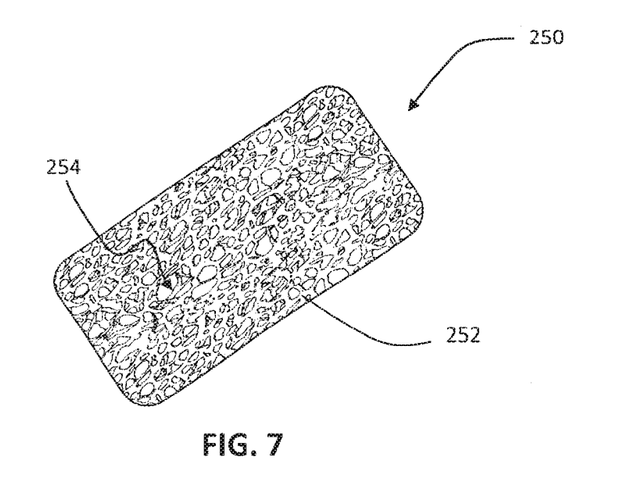
FIG. 7 is a plan view of a reticulated vitreous carbon (RVC) structure.

With reference to FIG. 7, for example, RVC structure 250 is provided in a block shape. RVC structure 250 includes a large plurality of vitreous carbon ligaments 252 that define open-cells or pores 254 therebetween. Also, RVC structure 250 is at least slightly larger in size than the negative space 236 of mold 230 (FIGS. 6A and 6B).

Continuing to step 112 of method 100 (FIG. 1), the implant manufacturer or another party shapes the RVC structure in the mold. Shaping the RVC structure may involve closing the mold around the RVC structure until the RVC structure takes on the shape of the mold's negative space (step 108), which also corresponds to the shape of the prosthesis model (step 106). The shaped RVC should be permanently shapeable, such that the shaped RVC structure maintains its new shape even after being removed from the mold.

During the shaping step 112 of method 100, the vitreous carbon ligaments of the RVC structure, especially the outer-most vitreous carbon ligaments, may break away from adjacent ligaments and expose the adjacent ligaments for further shaping. For example, when a plurality of ligaments intersect at a node to form a dodecahedron-shaped pore, an outer-most one of the ligaments may break away at the node, exposing the next ligament(s) at the node, which may correspond to the same pore as the broken ligament or an adjacent pore. In this manner, the outer-most surface of the RVC structure flakes away layer-by-layer during the shaping step 112. As a result, at least along the outer-most surface, the porosity of the RVC structure may remain substantially the same before and after the shaping step 112.

Periodically, the implant manufacturer may need to open the mold and remove the broken, powder-like struts from the mold (e.g., with a stream of compressed air) to accommodate further shaping in the mold. In this manner, the shaping step 112 may be an iterative process that involves, for example, (a) adjusting the mold to a first, partially closed position to initially shape the RVC structure, (b) opening the mold to remove broken struts, (c) adjusting the mold to a second, nearly closed position to further shape the RVC structure, (d) re-opening the mold to remove more broken struts, and (e) adjusting the mold to a third, fully closed position to fully shape the RVC structure.

Other vitreous carbon ligaments of the RVC structure, especially interior vitreous carbon ligaments, may become deformed and/or crushed in the mold. Therefore, it is within the scope of the present disclosure that the bulk porosity of the RVC structure may decrease during the shaping step 112. If necessary, excess material may be trimmed or otherwise removed from the shaped RVC structure after shaping the RVC structure in the mold.

Figure 8A:
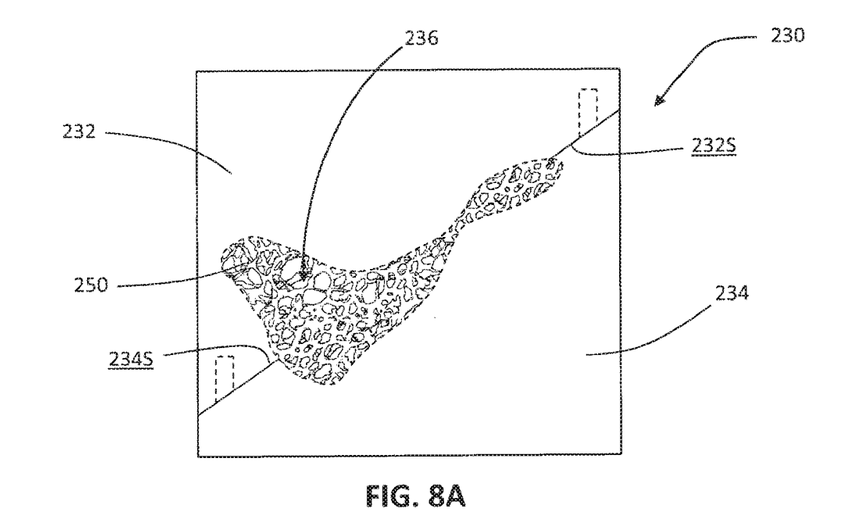
FIG. 8A is an elevational view of the mold of FIG. 6A being used to shape the RVC structure of FIG. 7, the mold shown in the closed position.
Figure 8B:
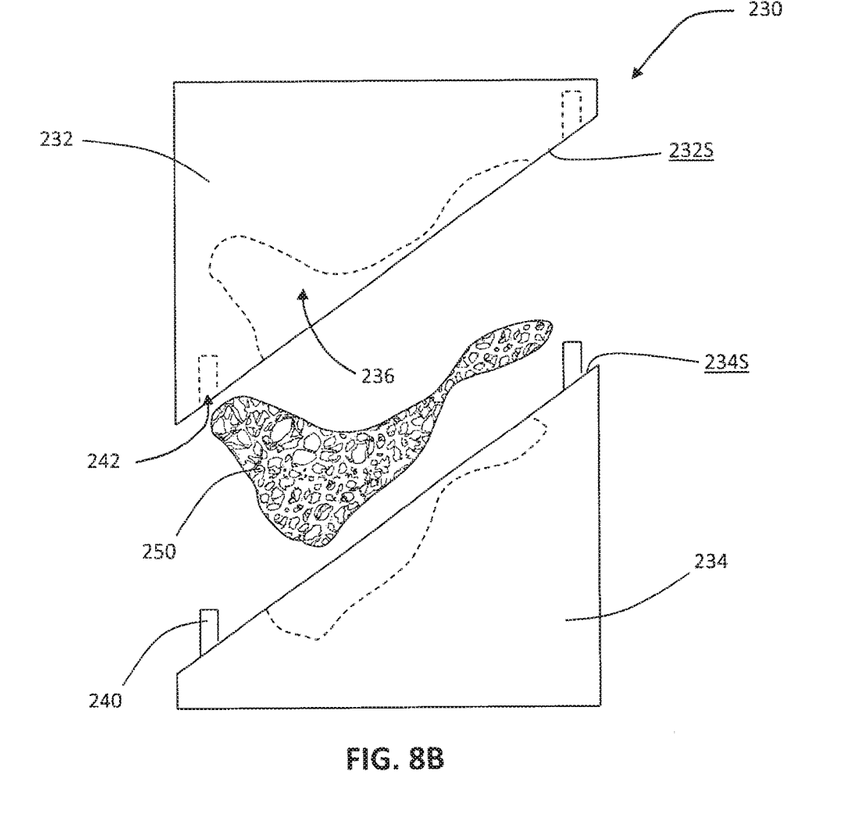
FIG. 8B is an elevational view similar to FIG. 8A, the mold shown in the open position to reveal the shaped RVC structure.

With reference to FIGS. 8A and 8B, for example, RVC structure 250 is enclosed between first and second portions 232, 234, of the illustrative mold 230. As interfacing surfaces 232S, 234S, of mold 230 move together, as shown in FIG. 8A, RVC structure 250 takes on the shape of the negative space 236 of mold 230, which also corresponds to the shape of prosthesis model 220 (FIGS. 4 and 5). First and second portions 232, 234, of mold 230 may be forced together and held together using a mechanical clamping device, for example. Even after being removed from mold 230, the shaped RVC structure 250 maintains its new shape, as shown in FIG. 8B.

According to an exemplary embodiment of the present disclosure, the amount of breakage, deformation, and/or crushing that occurs during step 112 (FIG. 1) is minimized for efficiency and to avoid substantially changing the porosity of the RVC structure. For example, the vitreous carbon ligaments of the RVC structure should remain sufficiently spaced apart to maintain the porous nature of the RVC structure. In practice, the amount of breakage, deformation, and/or crushing may be minimized by selecting an RVC structure during step 110 that is similar in size and shape to the mold's negative space, such that the RVC structure is able to take on the shape of the mold's negative space without requiring substantial breakage, deformation, and/or crushing. Also, the amount of breakage, deformation, and/or crushing may be minimized by designing the mold to compress the RVC structure in multiple, non-parallel directions.

Figure 9:
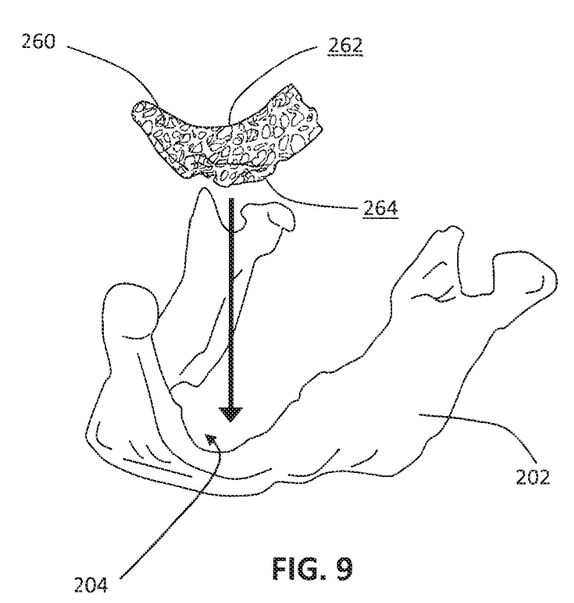
FIG. 9 is a perspective view of a patient-specific porous metal prosthesis being implanted onto the patient's damaged mandible.

Next, in step 114 of method 100 (FIG. 1), the implant manufacturer or another party coats the vitreous carbon ligaments of the shaped RVC structure with a biocompatible metal to produce a custom, patient-specific orthopaedic prosthesis. The coating step may strengthen the substrate for implantation, causing the substrate to become less readily shapeable than before the coating step. In this manner, the shaped RVC structure serves as a porous skeleton for the biocompatible metal coating. The orthopaedic prosthesis from step 114 corresponds in size and shape to the previously-designed prosthesis model from step 106. With reference to FIG. 9, for example, orthopaedic prosthesis 260 is provided that corresponds in size and shape to the previously-designed prosthesis model 220 (FIGS. 4 and 5).

Like its representative prosthesis model from step 106, the orthopaedic prosthesis from step 114 may be highly irregular, arbitrary, and biologically complex in shape. Such orthopaedic prostheses may be capable of use in geometrically demanding applications, such as craniomaxillio facial (CMF) surgeries or complex acetabular reconstruction surgeries. In certain embodiments, the orthopaedic prosthesis may lack any planes of symmetry. For example, as shown in FIG. 9, the shape of orthopaedic prosthesis 260 is highly irregular and lacks any planes of symmetry. Also, at least a portion of the outer surface of the orthopaedic prosthesis may be non-parametric in shape, such that the portion of the outer surface does not fall along a parametric line or curve. For example, as shown in FIG. 9, at least bone-contacting surface 264 of orthopaedic prosthesis 260 is non-parametric in shape. It is also within the scope of the present disclosure that the entire outer surface of the orthopaedic prosthesis may be non-parametric in shape. The orthopaedic prostheses produced according to method 100 may be distinguished from orthopaedic prostheses that are simple, regular, symmetric, geometric, or parametric in shape, such as hemispherical acetabular cups, cylindrical plugs, and pads having a consistent thickness, for example.

Suitable biocompatible metals for use during the coating step 114 of method 100 include, for example, tantalum, titanium, niobium, hafnium, tungsten, and alloys thereof. The shaped RVC structure may grow substantially uniformly during the coating step 114 as the metal is deposited onto the vitreous carbon ligaments, so it may be necessary for the shaped RVC structure to be slightly smaller in scale than the final orthopaedic prosthesis. Therefore, the mold that shapes the RVC structure may be slightly smaller in scale than the prosthesis model.

An exemplary method for coating the shaped RVC structure in step 114 of method 100 is a chemical vapor deposition (CVD) process. An exemplary CVD process is described in U.S. Pat. No. 5,282,861 to Kaplan, the disclosure of which is expressly incorporated herein by reference. During the coating step 114, the shaped RVC structure is placed inside a furnace and heated to a temperature of approximately 1100° C. Then, the shaped RVC structure is exposed to gaseous tantalum chloride ($TaCl_5$) and gaseous hydrogen ($H_2$), which react to produce solid tantalum metal. The resulting tantalum metal is deposited in a thin, substantially uniform film onto the outer vitreous carbon ligaments of the shaped RVC structure. Because the gaseous reactants are able to infiltrate the porous RVC structure, the resulting tantalum metal is also deposited in a thin, substantially uniform film onto the inner vitreous carbon ligaments of the shaped RVC structure. To promote even metal infiltration and deposition, the shaped RVC structure may be flipped and/or rotated during the CVD process or between individual cycles of the CVD process.

According to an exemplary embodiment of the present disclosure, the orthopaedic prosthesis produced by method 100 (FIG. 1) is a highly porous metallic structure, such as a highly porous tantalum structure, which may have a porosity as low as 55%, 65%, or 75% and as high as 80%, 85%, or 90%. Generally, the highly porous tantalum structure includes a large plurality of struts in the form of ligaments defining open-cells or pores therebetween, with each ligament generally including a vitreous carbon core covered by a thin film of tantalum metal. The open-cells between the ligaments form a matrix of continuous channels having no dead ends, such that growth of cancellous bone through the porous tantalum structure is uninhibited. The porous tantalum structure may include up to 75%-85% or more void space therein. Thus, porous tantalum is a lightweight, strong porous material which is substantially uniform and consistent in composition, and closely resembles the structure of natural cancellous bone, thereby providing a matrix into which cancellous bone may grow.

The porous tantalum structure may be made in a variety of densities in order to selectively tailor the structure for particular applications. In particular, as discussed in the above-incorporated U.S. Pat. No. 5,282,861, the porous tantalum structure may be fabricated to virtually any desired porosity and pore size, and can thus be matched with the surrounding natural bone in order to provide an optimized matrix for bone ingrowth and mineralization.

After the coating step 114 of method 100 (FIG. 1), the orthopaedic prosthesis may be subjected to any necessary shaping, processing, sterilizing, or packaging steps. For example, a polymeric bearing component may be secured onto the orthopaedic prosthesis to form an articulating, joint replacement implant. As another example, the orthopaedic prosthesis may be coupled to a solid metal substrate, such as by sintering or diffusion bonding.

Finally, in step 116 of method 100 (FIG. 1), the surgeon or another party implants the orthopaedic prosthesis into the patient's damaged bone. As discussed above, the orthopaedic prosthesis may be sized and shaped to replicate all or a portion of the patient's bone that will be resected and/or to fill in a missing portion of the damaged bone. Also, the orthopaedic prosthesis may be a rigid, strong, porous structure that stabilizes the patient's damaged bone and that provides a matrix for bone ingrowth. The surgeon may secure the orthopaedic prosthesis in place using suitable fasteners (e.g., bone screws) or bone cement, for example.

With reference to FIG. 9, for example, orthopaedic prosthesis 260 is shown being implanted onto the patient's damaged mandible 202 or lower jaw bone. The illustrative orthopaedic prosthesis 260 includes a proximal, exposed surface 262 and a distal, bone-contacting surface 264 that are sized and shaped to fill in bone loss area 204 of the patient's mandible 202. As discussed above, bone-contacting surface 264 is a patient-specific surface that is shaped as substantially a negative of the patient's damaged mandible 202 such that bone-contacting surface 264 of orthopaedic prosthesis 260 conforms to the patient's damaged mandible 202 and is perfectly contoured to fit against the patient's damaged mandible 202, even a substantially uncut or unreamed surface of the patient's damaged mandible 202 that is highly irregular, arbitrary, non-parametric, or biologically complex.

Figure 10:
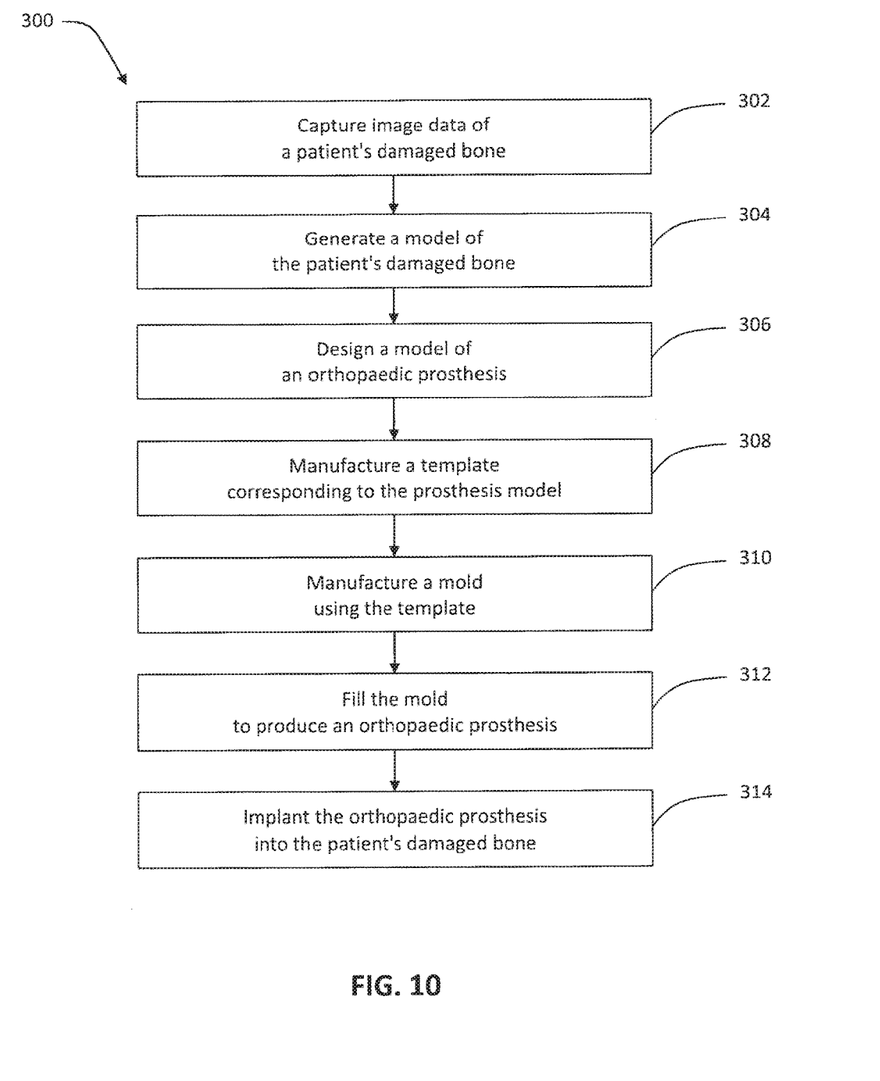
FIG. 10 is a flow chart of another exemplary method for designing and manufacturing a patient-specific prosthesis.

FIG. 10 provides another exemplary method 300 for designing and manufacturing a patient-specific prosthesis. Method 300 (FIG. 10) is similar to method 100 (FIG. 1), except as set forth below. Method 300 is exemplified with reference to FIGS. 11 and 12.

Method 300 (FIG. 10) begins like method 100 (FIG. 1). First, in step 302, a surgeon or another party captures image data of a patient's damaged bone. Then, in step 304, the surgeon or another party generates a three-dimensional model of the damaged bone. Next, in step 306, the surgeon or another party designs a custom, patient-specific prosthesis model. As discussed above, the prosthesis model may be designed to be highly irregular, arbitrary, and biologically complex in shape to accommodate the traumatic injury or deterioration suffered by the particular patient and the surrounding anatomy of the particular patient.

Continuing to step 308 of method 300 (FIG. 10), an implant manufacturer or another party manufactures a custom, patient-specific template having substantially the same size and shape as the prosthesis model from step 306. In an exemplary embodiment, the template is manufactured using a rapid additive or subtractive manufacturing process. As discussed further above, the rapid additive manufacturing process may include 3-D printing, selective laser sintering, or fused deposition modeling, for example. Such manufacturing methods enable automatic and rapid construction of a custom, patient-specific template in step 308 that will mimic the highly irregular, arbitrary, and biologically complex prosthesis model from step 306.

Figure 11:
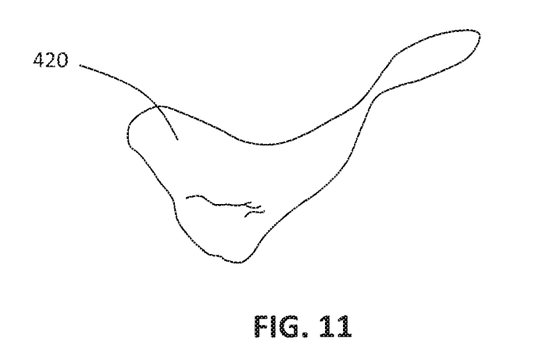
FIG. 11 is an elevational view of a rapid-prototyped template having substantially the same size and shape as the prosthesis model of FIG. 4.

With reference to FIG. 11, for example, a custom, patient-specific template 420 is manufactured having substantially the same size and shape as prosthesis model 220 (FIGS. 4 and 5). Template 420 may be manufactured of a polymer, metal, or another suitable material.

In step 310 of method 300 (FIG. 1), the implant manufacturer then makes a custom, patient-specific mold using the template from step 308. In an exemplary embodiment, the mold itself is manufactured by a casting or molding process, with the template from step 308 defining the interior shape of the mold and another template defining the exterior shape of the mold. Forming elements like pins and dividers may also be used to add openings, injection ports, and other features to the mold. When the templates and other forming elements are separated from the newly cast mold, the negative space of the mold will be sized and shaped to match the template (step 308) and the prosthesis model (step 306). In this manner, the mold will be capable of producing a part having substantially the same size and shape as the prosthesis model (step 306).

Figure 12:
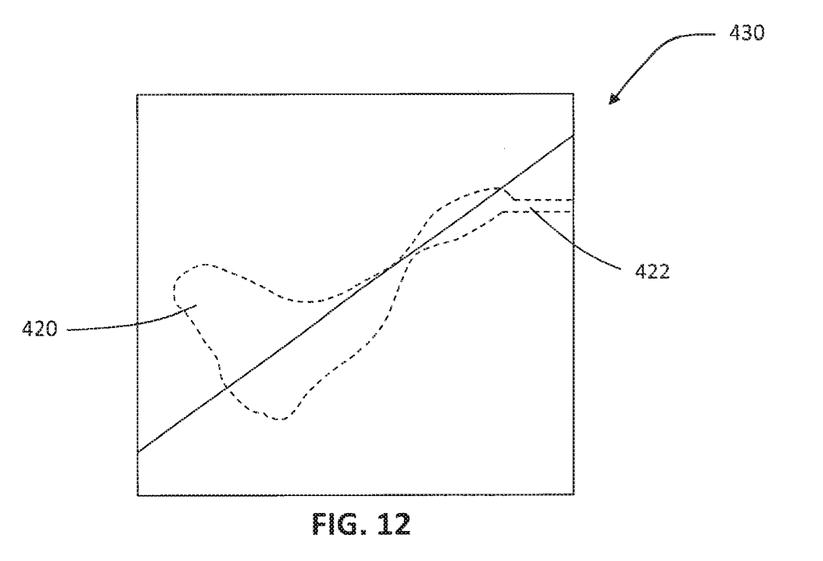
FIG. 12 is an elevational view of a mold being formed around the template of FIG. 11.

With reference to FIG. 12, for example, a custom, patient-specific mold 430 is manufactured with template 420 defining the interior shape of mold 430 and a second, outer template (not shown) defining the exterior shape of mold 430. Pin 422 extends into mold 430 to define an injection port in mold 430. When template 420 and pin 422 are removed from the newly cast mold 430, the negative space of mold 430 will be sized and shaped to match template 420 (FIG. 12) and prosthesis model 220 (FIGS. 4 and 5).

Next, in step 312 of method 300 (FIG. 10), the implant manufacturer fills the mold from step 310 with a biocompatible material to produce a custom, patient-specific orthopaedic prosthesis. The filling step 312 may involve an injection molding process, for example. When the orthopaedic prosthesis is dried and removed from the mold, the orthopaedic prosthesis will retain the shape of the mold's negative space (step 310), which also corresponds to the shape of the template (step 308) and the prosthesis model (step 306).

In one embodiment, the biocompatible material used in the molding step 312 is a metal. Suitable metals include, for example, titanium, tantalum, cobalt chromium, cobalt chromium molybdenum, and alloys thereof.

In another embodiment, the biocompatible material used in the molding step 312 is a polymer. The polymer may be pre-polymerized before being injected into the mold. Such pre-polymerized materials include, for example, polyurethane, polystyrene, polypropylene, polyethylene, and polyoxymethylene. Alternatively, unpolymerized materials may be injected into the mold with polymerization occurring in the mold. Such unpolymerized materials include polyisocyanates and polyols, for example, which will react in the mold to form a polymer. For added strength, the polymer may be further processed and coated with metal following the molding step 312. An exemplary process is described above in step 114 of method 100 (FIG. 1) and in European Patent Application Serial No. EP 10014692.7, entitled "Porous Metal Structures Made from Polymer Preforms," filed on Nov. 17, 2010, the entire disclosure of which is expressly incorporated herein by reference.

To produce a porous orthopaedic prosthesis, a void former may be used during the molding step 312. The void former may include, for example, removable grains or particles, a blowing agent, or a chemical reactant. The void former will leave behind spaces or pores in the orthopaedic prosthesis.

Finally, in step 314 of method 300 (FIG. 10), the surgeon or another party implants the orthopaedic prosthesis into the patient's damaged bone.

It is also within the scope of the present disclosure that the biocompatible material that is inserted into the mold is a shapeable substrate, as discussed above with respect to FIGS. 1-9. The substrate may be shaped in the mold by breakage, deformation, and/or crushing, and then the shaped substrate may be coated and implanted, as discussed above.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing patient-specific orthopaedic prosthesis using prosthesis model that is shaped to represent the patient-specific orthopaedic prosthesis, the method comprising the steps of:
    manufacturing a patient-specific mold that defines negative space, the negative space of the patient-specific mold corresponding in shape to the prosthesis model;
    selecting porous substrate having plurality of struts that define pores of the porous substrate, the porous substrate having first shape being slightly larger than the negative space defined by the patient-specific mold, wherein the negative space of the patient-specific mold is configured to compress the porous substrate in multiple, non-parallel directions;
    operating the patient-specific mold to compress the first shape of the porous substrate in the multiple, non-parallel directions to a second shape that differs from the first shape, the second shape of the porous substrate corresponding to the prosthesis model; and
    after the operating step, coating the plurality of struts of the porous substrate with biocompatible metal.

2. The method of claim 1, wherein the first shape is regular shape and the second shape is an irregular shape.

3. The method of claim 1, wherein the first shape is symmetrical shape and the second shape is an asymmetrical shape.

4. The method of claim 1, wherein at least a portion of the pores decrease in size during the operating step.

5. The method of claim 1, wherein at least a portion of the pores decrease in size during the coating step.

6. The method of claim 1, wherein the porous substrate is more readily shapeable before the coating step than after the coating step.

7. The method of claim 1, wherein the manufacturing step comprises performing rapid manufacturing process the rapid manufacturing process including one of an additive process and subtractive process.

8. The method of claim 7, wherein the rapid manufacturing process comprises at least one of 3-D printing selective laser sintering and fused deposition modeling.

9. The method of claim 1, wherein operating the patient-specific mold to compress the porous substrate with the patient-specific mold permanently deforms, breaks, or crushes a portion of the plurality of struts of the porous substrate to reshape the porous substrate.

10. The method of claim 1, further comprising the step of obtaining image data of a patient's damaged bone;
    designing the prosthesis model from image data of the patient's damaged bone, the prosthesis model being representative of the custom, patient-specific orthopaedic prosthesis.

11. The method of claim 1, wherein the negative space of the patient-specific mold is smaller in scale than the prosthesis model to account for a size increase that occurs during the coating step.

12. The method of claim 1, wherein the porous substrate comprises reticulated vitreous carbon.

13. The method of claim 1, wherein the patient-specific mold is manufactured by a first party and the shaping step is carried out by a second party.

14. The method of claim 1, wherein operating the patient-specific mold to compress the porous substrate includes opening the mold to remove broken powder-like struts from the mold to accommodate further shaping in the patient-specific mold.

15. A method of manufacturing patient-specific orthopaedic prosthesis using prosthesis model that is shaped to represent the patient-specific orthopaedic prosthesis, the method comprising the steps of:
    manufacturing a patient-specific mold that defines negative space, the negative space of the patient-specific mold corresponding in shape to the prosthesis model;
    selecting porous substrate having plurality of struts that define pores of the porous substrate, the porous substrate having first shape being slightly larger than the negative space defined by the patient-specific mold;
    iteratively operating the patient-specific mold to compress the first shape of the porous substrate to a second shape that differs from the first shape, the second shape of the porous substrate corresponding to the prosthesis model, wherein the iteratively operating the patient-specific mold includes at least adjusting the patient-specific mold to a first, partially closed position to initially shape the porous substrate, opening the mold to remove broken struts and adjusting the patient-specific mold to a second position to further shape the porous substrate; and
    after the operating step, coating the plurality of struts of the porous substrate with biocompatible metal.

16. The method of claim 15, further comprising opening the mold to remove broken struts and adjusting the patient-specific mold to a third, fully closed position to fully shape the porous substrate to the second shape.

17. The method of claim 15, wherein operating the patient-specific mold to compress the porous substrate with the patient-specific mold permanently deforms, breaks, or crushes a portion of the plurality of struts of the porous substrate to reshape the porous substrate.

18. The method of claim 15, wherein the negative space of the patient-specific mold is configured to compress the porous substrate in multiple, non-parallel directions.

* * * * *